United States Patent [19]
Galkin et al.

[11] 4,307,713
[45] Dec. 29, 1981

[54] SYRINGE SHIELDS AND METHODS FOR USING SAME

[75] Inventors: Benjamin M. Galkin, Cherry Hill, N.J.; Raymond Boon, Glenolden, Pa.; Rudolph V. Gilliam, Yeadon, Pa.; Chan H. Park, Ambler, Pa.

[73] Assignee: Thomas Jefferson University, Philadelphia, Pa.

[21] Appl. No.: 121,211

[22] Filed: Feb. 13, 1980

[51] Int. Cl.³ .............................................. A61B 6/00
[52] U.S. Cl. ..................................... 128/1.1; 250/506
[58] Field of Search ................. 128/1.1, 215; 250/506, 250/496, 497

[56] References Cited
U.S. PATENT DOCUMENTS

| | | | |
|---|---|---|---|
| 3,993,063 | 11/1976 | Larrabee | 128/215 |
| 4,056,096 | 11/1977 | Collica et al. | 128/1.1 |
| 4,060,073 | 11/1977 | Collica et al. | 128/1.1 |
| 4,122,836 | 10/1978 | Burnett | 128/1.1 |

Primary Examiner—John D. Yasko
Attorney, Agent, or Firm—Woodcock, Washburn, Kurtz, Mackiewicz & Norris

[57] ABSTRACT

The present invention relates to syringe loading shields for use with syringes during the drawing of aliquots of radioactive materials from shielded vials containing same. Each syringe loading shield is provided with means for shielding radiation emanating from the mouth of the vial during the material-withdrawal, syringe loading process. In a preferred embodiment, the syringe loading shield comprises a radiation detector for detecting and calibrating the radioactive dosage of the material which is drawn into the syringe barrel. In the preferred embodiment, a substantially tubular shield having a high density viewing window recessed therein is disclosed which is comprised of a plurality of sheaths. A novel hand shield and syringe for use with radioactive materials are also disclosed.

11 Claims, 5 Drawing Figures

SYRINGE SHIELDS AND METHODS FOR USING SAME

BACKGROUND OF INVENTION

The present invention relates generally to the field of radiation shielding equipment, and more particularly, to shields for use by radio-pharmacists while withdrawing aliquots of radioactive materials contained within shielded vials.

It has long been known to shield syringes containing radioactive materials. Heretofore, such syringes have been shielded by devices which generally surround the syringe barrel, while permitting the needle and needle hub of the syringe to extend beyond the end of the shield. Means have been provided in these shields for holding the syringe more or less securely within the shield. Some syringe shields have incorporated a high density glass to facilitate viewing of the syringe markings and contents. In U.S. Pat. No. 3,820,541 a shield for a hypodermic syringe is disclosed which is lead lined and is provided with a bayonet fitting element engaging the manually engaged end of the syringe. A coil spring cooperates with the bayonet fitting element to prevent wobbling between the barrel of the syringe and the barrel of the shield. The barrel of the shield is so configured that a small end of the barrel of the syringe is uncovered to permit visual inspection of flow to and from the syringe.

In U.S. Pat. No. 4,062,353 dated Dec. 13, 1977 a syringe shield is disclosed which is characterized in the provision of a removable, arcuately shaped bushing positionable in the bore of the shield for decreasing the effective diameter thereof to support a syringe barrel against a single set screw. The bushing is inserted with the syringe barrel into an oversized bore in the shield permitting passage of the needle of the syringe with an intact needle cover, thereby maintaining the sterility of the needle.

While most prior art syringe shields provide good finger and hand protection from the radiation coming from within the syringe, such shields normally offer little or no protection from the radiation coming from the mouth of the vial from which the radioactive material is drawn. Even though most such vials are fitted with vial shields, when the covers of those shields are removed and the vial inverted for dosage withdrawal, little or no protection is provided against radiation emanating from the mouth of the dosage vial. Further, since most dosage vials contain multiple dosages of radioactive materials, it may readily be appreciated that the amount of radiation emanating from a dosage vial is normally many times greater than that emanating from a syringe containing a single dosage of the subject material. Further, in view of the orientation of the dosage vial during withdrawal of the radioactive material, the radiation emanating from the dosage vial normally extends over a much greater area of the hand than that emanating from the subject syringe.

The high density viewing glass of state of the art syringe shields tends to be easily broken and/or dislodged from its setting in the syringe shield barrel. These windows normally project from the exterior surface of these syringe shields, and thus are particularly prone to breakage, etc. Finally, a thick viewing glass makes observation of the volumetric markings on a syringe disposed within the shield difficult to read, particularly against a metallic background which is often the color of the oxides of lead or tungsten.

According to state-of-the-art methods, it is desirable to measure and calibrate the radioactive dosage of an aliquot which has been withdrawn from a dosage vial into the syringe, prior to the injection of that material into a patient. This is normally accomplished by inserting the loaded syringe (without syringe shield) into a dose calibrator which measures the amount of radioactivity contained within the syringe. Since most radio-pharmacists are acutely aware that their total radiation exposure is as dependent upon the time of exposure as it is upon the intensity of that exposure, most radio-pharmacists prefer to work quickly with radioactive materials. Since state of the art syringe shields, even if used during the withdrawal of material from the dosage vial, must be removed in order to calibrate dosage, many radio-pharmacists omit the use of any syringe shield, at least until after calibration has been completed.

SUMMARY OF THE INVENTION

The present invention provides a novel syringe shield for use with a syringe at least during the loading of that syringe with aliquots of radioactive materials drawn from the mouth of a dosage vial which is otherwise protected by a conventional vial shield. The present invention provides a syringe shield and hand shield, each of which is constructed to shield the user from radiation emanating from the mouth of the dosage vial during the loading of the syringe. In the preferred embodiment, a syringe shield is provided having a substantially tubular body for receiving at least the barrel portion of the syringe, and a mouth shield means connected to and extending transversely away from that body to substantially shield the mouth of the vial at least during the drawing of said aliquots. In the preferred embodiment, the mouth shield is a substantially annular flange which is sized to cover and overlap at least that portion of the vial shield which surrounds the mouth of the dosage vial. The tubular body preferably also surrounds the needle hub and a portion of the needle.

The present invention also provides a syringe shield which is intended to eliminate the necessity of removing a loaded syringe from its shield for transfer to a separate dosage calibration apparatus. In the preferred embodiment, a radiation detector is disposed within the tubular body of the syringe shield, which detector is connected to a remote dosage calibrator which is capable of calculating and indicating the dosage which has been loaded into the syringe.

The preferred embodiment syringe shield further comprises a body having a plurality of sheaths: a non-toxic exterior sheath, an intermediate shielding sheath, and an interior optically-contrasting sheath which contrasts with the volumetric markings of a syringe contained within the shield. This laminar construction enables a high-density viewing window to be recessed within the body of the shield, to thereby reduce the likelihood that the window will be broken or dislodged from its mounting.

In alternate embodiments of the present invention, means are provided for interconnecting the syringe shield to a modified vial shield, and for temporarily retaining the syringe within the syringe shield during the syringe loading process.

The present invention also provides a novel syringe which is otherwise made of low density materials, but contains a "barrel" shield which is connected to the syringe plunger and which shields radiation directed generally co-axially along the syringe barrel.

An extremely simple hand shield is also disclosed which comprises a disc having an aperture therethrough for receiving the barrel of a given syringe, and which may be used during the syringe loading process to protect the fingers and hand of the user.

As seen from the above, a primary object of the present invention is the provision of apparatus which reduces the exposure of a radio-pharmacist to radiation during the loading of syringes with radioactive materials and/or the calibration of dosages contained within those syringes.

Another object of the present invention is the provision of novel methods for loading and calibrating syringes containing radioactive materials.

These and other objects of the present invention will become apparent from the following more detailed description.

BRIEF DESCRIPTION

DETAILED DESCRIPTION OF DRAWINGS

It will be understood that while various examples and embodiments of the present invention have been selected for the purpose of illustration in connection with the following description and figures, these embodiments, examples and figures are representative and not intended to limit the scope of the present invention, which is defined in the appended claims.

Figure 1:
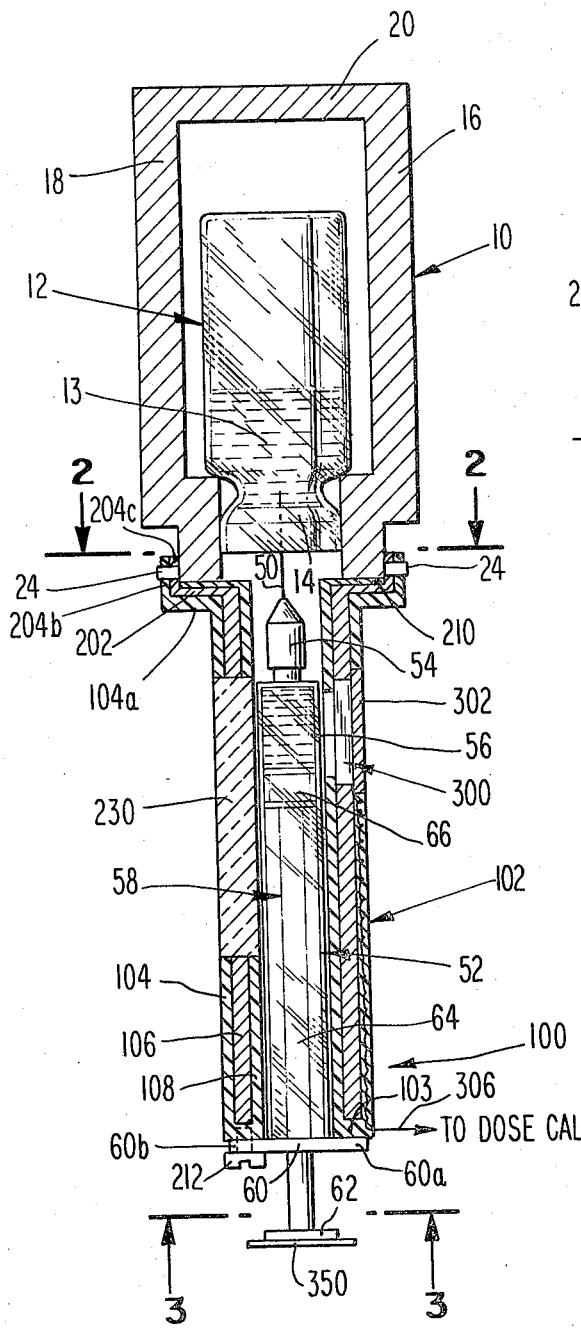
FIG. 1 is a cross-section of the preferred embodiment syringe loading shield of the present invention shown in its engaged position with a modified vial shield containing a dosage vial, and further showing the retention of a syringe in that shield.
Figure 2:
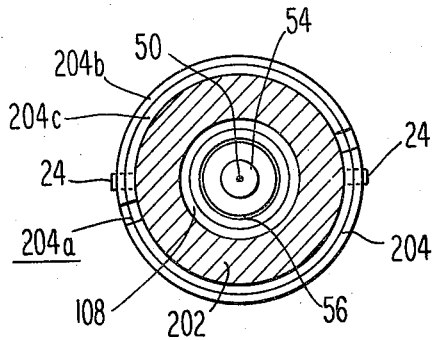
FIG. 2 is a cross-section of the apparatus depicted in FIG. 1 taken along the lines and arrows 2—2 in FIG. 1.
Figure 3:
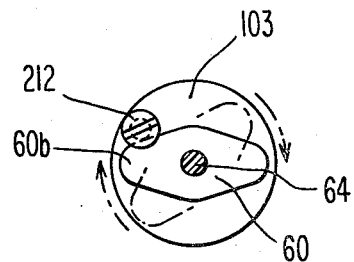
FIG. 3 is a cross-section of the apparatus shown in FIG. 1 taken along the lines and arrows 3—3 in FIG. 1, showing the rotation of the syringe between free and retained positions.

The preferred embodiment syringe loading shield of the present invention comprises a tubular body, a mouth shield extending transversely away from the body for a preselected distance to substantially shield the mouth of an associated dosage vial, and a radioactive material detection means disposed within said body for detecting the radioactivity of the aliquot drawn into the barrel of the syringe. Referring now to the drawings, and particularly FIGS. 1-3, the preferred embodiment syringe shield is shown associated with a modified vial shield, designated generally 10, within which is disposed a multi-dose vial, designated generally 12, containing liquid radioactive material 13 which may be withdrawn through a conventional vial stopper 14. The vial shield 10 comprises shielding walls 16 and 18, a shielding base 20, and an annular shielding collar 22 which defines a vial shield mouth within which the multidose vial stopper 14 is disposed to permit access and penetration by the syringe needle 50. The vial 12 is held in its illustrated position within the vial shield 10 in a conventional manner, such as by use of vial shield spacer (not illustrated).

The multi-dose vial shield 10 illustrated in FIG. 1 has been modified to the extent that it has been provided with a plurality of pins 24 which are mounted on the collar 22 and which engage, in a bayonet-type manner, a scatter shield portion of the preferred embodiment syringe loading shield, as described more fully hereinafter.

The preferred embodiment syringe loading shield is intended for use with a modified disposable syringe designated generally 52. This syringe 52 comprises a needle 50, needle hub 54, syringe barrel 56, a plunger, designated generally 58, and a syringe base 60 which extends beyond the outer edges of the syringe barrel 56 to define finger-flange portions 60a and 60b. In the preferred embodiment, the plunger, designated generally 58, comprises a thumb flange 62, plunger shaft 64 and piston 66.

The preferred syringe loading shield, designated generally 100, comprises a body means for receiving at least the barrel portion of the syringe 52 so that the barrel of the syringe will be entirely contained within the body, as will syringe hub 54 and a portion of needle 50. This syringe shield is sized so that its base 103 will interfere with finger flanges 60a and 60b to prevent the syringe from being over-inserted into the shield, while establishing a syringe position where needle 50 penetrates through stopper 14 of the dosage vial 12 so that aliquots of material may be withdrawn from the vial. In this preferred embodiment, the body means is a substantially tubular body, designated generally 102, which comprises an exterior sheath 104, intermediate sheath 106 and interior sheath 108. Preferably, the exterior sheath 104 and interior sheath 108 consist of non-toxic, low density materials, such as aluminum, polytetrafluoroethylene, (Teflon ®), polypropylene, polyethylene, or other suitable plastic materials. The intermediate sheath, 106, is preferably a shielding material, such as lead, tungsten or copper, which is isolated from the environment by its encapsulation in the aforementioned exterior and interior sheaths.

Disposed at the end of the tubular body 102 which is in proximity with the dosage vial is a mouth shield means which extends transversely away from the body means for a preselected distance to substantially shield at least the mouth of the vial during at least the withdrawal of aliquots of radioactive materials. In the preferred embodiment, this mouth shield means comprises an annular mouth shield flange 202 which is sized not only to cover the mouth of the multi-dose vial 12, but also to extend over and to cover the mouth of the vial shield 10 and the vial shield collar 22. In order to insure that lateral scatter which might otherwise occur from between the collar 22 and mouth shield flange 202 is prevented, a lateral scatter shield is provided which extends away from the mouth shield flange 202 to surround at least a portion of the collar 22 of the vial shield. As seen in FIG. 1, a cylindrical, projecting scatter shield ring 204 is illustrated which is substantially coaxial with the tubular body 102 of the syringe loading shield and which extends for a preselected distance along the sides of vial shield collar 22.

During normal use, it is not anticipated that the syringe loading shield 100 and vial shield 10 must be interconnected by the radio-pharmacist during their use. In fact, experience has indicated that most radio-pharmacists prefer to simply manually position the vial shield 10 and syringe shield 100 as shown in FIG. 1. Some radio-pharmacists may, however, desire to removably connect the syringe loading shield 100 to a given vial shield for purposes of convenience or improved safety. As shown in FIG. 1, therefore, the scatter shield means may comprise a vial-shield interconnection means which removably retains the syringe shield in a preselected position relative to the vial shield. As shown particularly in FIG. 2, the scatter shield projecting ring 204 may be provided with one or more bayonet slots 204a which are adapted to receive and, upon rotation, to engage the aforementioned vial shield pins 24 to accomplish that retention.

In the preferred embodiment, a portion of 204b the scatter shield projecting ring 204 may comprise an extension of the exterior sheath 104 of the syringe loading shield. In FIG. 1, this sheath is seen to extend laterally to define mouth shield covering portion 104A, and to form the aforementioned scatter shield ring portion 204b. This construction is preferred when the exterior sheath 104 is composed of a material, such as aluminum, which possesses suitable strength, rigidity and durability. The scatter shield ring 204a should in every event comprise at least one layer 204b of high density material, which may comprise an extension of the mouth shield material 202.

The surface of the mouth shield 200 which is exposed towards the vial shield 10 should be covered by an annular disc which is non-toxic and which, when brought in contact with the collar 22 of the vial shield, will not damage that collar. In the preferred embodiment, this mouth shield cover 210 may also be aluminum, or one of the other aforementioned plastic materials.

In this preferred embodiment, the finger flanges 60a and 60b not only define the syringe insertion distance by interferring with shield base 103, but also, upon rotation of the syringe, cooperate with a retaining means for selectively retaining the syringe barrel to at least prevent the axial movement of said barrel during the drawing of aliquots from the multi-dose vial 12. This retaining means comprises a locking means for receiving one of said finger flanges upon rotation of the syringe base 60. This is accomplished by providing a slot defining member located at the end of the syringe loading shield which is remote from the aforementioned mouth shield. In the embodiment illustrated in FIG. 1, this slot defining member is a panheaded screw 212 which is shown receiving and retaining finger flange 60b. This interrelationship, and the rotation of syringe base 60, are particularly well illustrated in FIG. 3 of the drawings.

In the embodiment illustrated in FIG. 1, the tubular body 102 defines a viewing aperture extending generally co-axially along the syringe barrel. A high density viewing window 230 is shown recessed in that aperture and is seen to substantially fill that aperture. The inner and the outer surfaces of this high density viewing window 230 are substantially co-planer with the cylindrical planes defined by the respective exterior and interior surfaces of the exterior sheath 104 and interior sheath 108. In this manner, the high density viewing window 230 neither projects into the central bore of the syringe loading shield, nor outwardly from the exterior of that shield. Accordingly, this window is not prone to dislodgement or breakage during routine use of the syringe loading shield. Alternatively, a viewing glass may be selected having a thickness which is approximately equal to the thickness of the exterior and intermediate sheaths 104 and 106, in which case a ledge of interior sheath material 108 may extend into the viewing aperture to provide an annular viewing glass mounting surface.

Dosages of radioactive materials are normally measured through volumetric indications on the syringe barrel, such as syringe barrel 56, as well as by detecting the amount of radiation emitted from a loaded syringe which has been transferred to a dosage calibrator. In the preferred embodiment, the portion of the interior sheath 108 which is disposed opposite to the viewing aperture is made of a material which optically contrasts with the volumetric markings on the syringe to be used. White polytetrafluoroethylene is a material of choice. Polytetrafluoroethylene (Teflon ®) is a low density material. Polytetrafluoroethylene is also a material possessing a very low sliding frictional resistance, thereby readily facilitating the insertion and removal of a syringe into the bore of a syringe shield lined with this material.

In order to accomplish the dose calibration of radioactive materials loaded into the barrel 56 of the syringe, the preferred embodiment syringe loading shield is provided with a radioactive material detection means which is disposed within the body means for detecting the radioactivity of the aliquot drawn into the barrel of the syringe. In the preferred embodiment, this radioactive material detection means is connected to a dosage calibration means for calibrating and indicating the dosage of radioactive materials contained within the syringe. This radioactive material detection means is preferably disposed adjacent to and coaxially along the syringe barrel 56 in its loading position. The preferred detection means comprises a detector designated generally 300 which may be located between the interior sheath 108 and the outer sheath 104. If necessary, in the vicinity of the radiation detector 300, a portion of the outer sheath 104 may be replaced with a shielding plate 302, which may be removable for purposes of assembling and/or servicing the radiation detector 300.

Radiation detector 300 may comprise any one of a number of such detectors known to the art. At the present time, the preferred radiation detector comprises a radio-fluorescent material which is disposed adjacent to the syringe barrel mounted on a ledge of the interior sheath material 108, which has a detection aperture defined therein. This radio-fluorescent material may be encapsulated in an appropriate low density container, if desired, for insertion into the position shown for radiation detector 300. In this instance, the preferred dosage calibration means comprises a light transmission means for transmitting light generated by the radio-fluorescent material in the presence of a source of radiation. Remote light quantification means may then be used for determining and indicating the dosage of material which is contained in the barrel of the syringe, as detected by the radiation detector. In FIG. 1, the means for transmitting information from the radiation detector 300 to such a remote location is diagrammatically illustrated by line 306.

An alternative radiation detector 300 which may be used in accordance with the present invention is an ionization-chamber radiation detector. In this instance, the output from the radiation detector 300 is electrical, and the mode of transmission of that information is by a wire or wires which are represented diagrammatically by line 306. A further alternate embodiment radiation detector is a solid state radiation detector. Once again, the transmission of information to the remote calibrator and indicator is by wires which are diagrammatically illustrated by line 306.

The preferred embodiment syringe loading shield is particularly adapted for use with a modified syringe which, in combination with the syringe loading shield, helps to shield the user of the syringe from any substantial radiation exposure. This preferred embodiment syringe is illustrated as syringe 52 in FIG. 1, and comprises a low density barrel 56, a low density plunger 58 slidingly disposed within said barrel, and a plunger shield means 350 connected to said plunger for shielding radiation transmitted within said barrel towards the user of said syringe. In the preferred embodiment, this plunger shield means is applied over the end of the plunger which is proximate to the user, that is, it is applied over the thumb plate 62 of the plunger, as for example through application of an adhesive material therebetween. The plunger shield means 350 should have a diameter which is at least as great as the inner diameter of the syringe barrel 56, and less than the maximum diameter of the syringe base 60. In its preferred form, the plunger shield means 350 is a disc of lead, tungsten, copper or other material, which may be coated or treated to prevent toxic contamination of the user. The half value layer of this shield may be from 1-5, preferably about 3.

In another alternate embodiment of the present invention, the plunger shield means may be connected to the plunger 58 at other locations, either along the plunger shaft 64 or as a part of, or encapsulated in, the piston 66. When the plunger shield means is disposed within the barrel 56 of the syringe, it is necessary to guard against any contamination of the materials to be drawn into the syringe. For this reason, it may be preferred to provide a disc or plug of shielding material which is entirely encapsulated in or enclosed by the syringe piston.

As seen in FIGS. 1-3, a simple, reliable, and well shielded syringe loading shield is disclosed which effectively reduces the likelihood that its user may be exposed to unacceptable levels of radiation during syringe loading processes.

Figure 4:
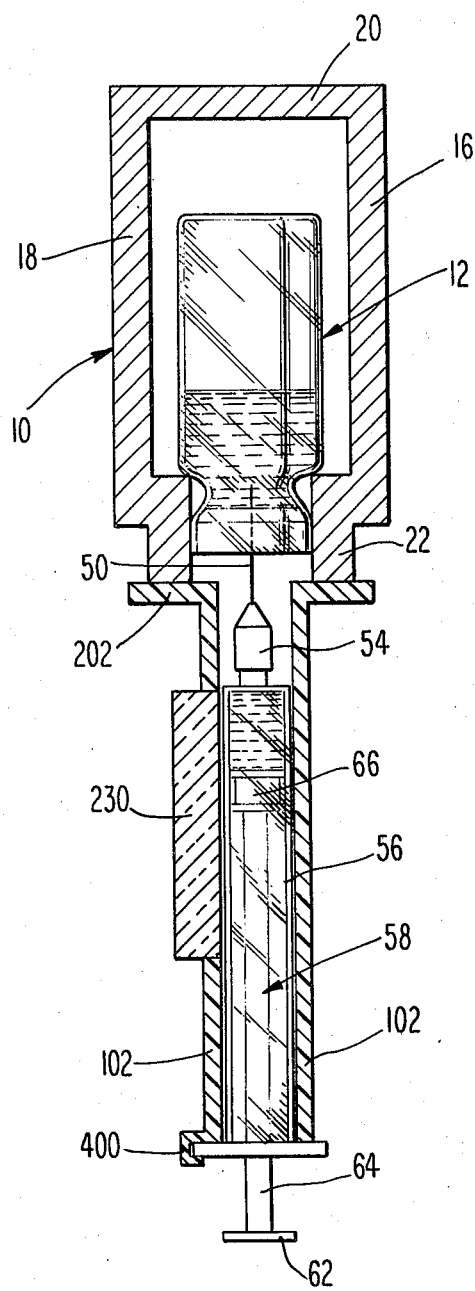
FIG. 4 is a cross-section of an alternate embodiment syringe loading shield shown with a syringe retained therein which is being loaded from a multidose vial contained within a conventional multidose vial shield.

Referring now to FIG. 4, an alternate embodiment, low-cost syringe loading shield is disclosed which possesses many of the advantages of the preferred embodiment syringe loading shield illustrated in FIGS. 1-3. For purposes of simplicity, corresponding portions of this embodiment have been numbered with the same numbers which were used in connection with the embodiment illustrated in FIGS. 1-3. It will be noted that in this embodiment, the syringe shield body 102 and mouth shield 202 comprise a single layer of shielding material. In this embodiment, an alternate embodiment slot-defining-member 400 is disclosed which comprises a U-shaped extension of a portion of the tubular body 102. It should be noted that the tubular body of the syringe loading shield surrounds the entire length of the barrel 56 of the syringe, the hub 54 of the needle, and a portion of the needle 50. The annular mouth shield 202 of the embodiment of FIGS. 1-3 has been retained to substantially shield the mouth of the vial shield 10, however, for purposes of economy the embodiment of FIG. 4 does not contain any means for creating a removable connection between the illustrated syringe loading shield and the vial shield. The mouth shield 202 nonetheless extends across a portion of the mouth of the multi-dose vial and across the collar 22 of the vial shield to terminate slightly therebeyond. It is anticipated that the outer diameter of the mouth shield 202 should not be any greater than about the outside diameter of the vial shield 10.

The syringe shield illustrated in FIG. 4 may also be modified for use during the injection of materials into a patient, provided the mouth shield is omitted therefrom and the tubular body is terminated, so that just the tip of the needle hub and needle are not surrounded by the body 102. In fact, when an optically transparent needle hub is utilized with this modified shield, it is possible for the individual administering the injection to observe the color of material within the transparent hub to insure that the needle is located within a vein of the patent. This is accomplished by observing for the color of blood which is drawn back through the needle into the needle hub 54. Accordingly, an alternate embodiment syringe shield is provided which may be used after dose calibration and during transport and injection of the calibrated dose to the patient. Unlike most prior art syringe shields, this alternate embodiment does not require any high density viewing glass, such as glass 230, and provides substantial shielding not only around the syringe barrel, but also throughout the syringe hub area.

Figure 5:
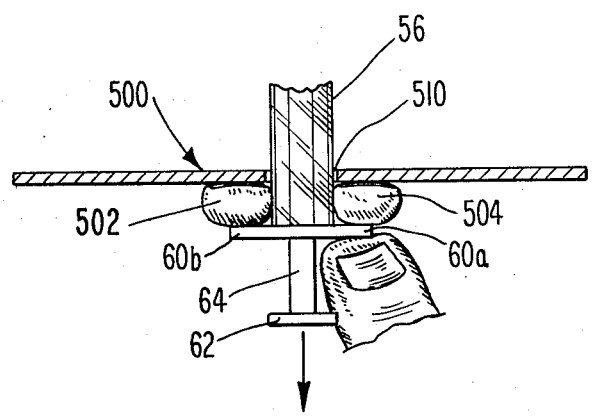
FIG. 5 is a cross-section of a preferred embodiment hand shield illustrating the orientation of a fragmentary portion of the base of a syringe and the tips of two of the user's fingers in their associated use position.

Referring now to FIG. 5, a further alternate embodiment hand shield is disclosed which may be used in lieu of the syringe loading shields hereinbefore described. This hand shield comprises a disc of shielding material having a syringe aperture 510 defined centrally therein. In FIG. 5, a cross-section of this hand shield, designated generally 500, is illustrated showing that shield in association with a foreshortened syringe barrel 56, finger flanges 60a and 60b, plunger shaft 64 and thumb plate 62. The tips of the two fingers, such as index and middle fingers 502 and 504, of the user are shown disposed between adjacent portions of finger flanges 60a and 60b and a contiguous portion of the hand shield 500. As used, the syringe is slipped through the aperture 510 of the shield 500 prior to loading. The syringe shield 500 is then balanced along the upper surfaces of the fingers of the user so that it is in a substantially horizontal position while the syringe itself is in a substantially vertical position ready for the insertion of its needle through the stopper of a multi-dose vial for withdrawal of an aliquot of material. This material may then be withdrawn, the needle removed from the vial, and the hand shield-syringe assembly transferred to a dose calibrator, whereupon the syringe may be quickly removed from the shield.

The disc 500 may be provided with additional outer layers in order to counteract the toxicity of the selected shielding material and/or to improve its appearance or rigidity, as desired. These covering materials may be stainless steel, or other materials similar to those disclosed for the exterior and interior sheaths of the embodiment of FIGS. 1-3.

It is preferred that the central aperture 510 defined in the disc 500 be of a sufficient diameter to easily permit the insertion and withdrawal of the subject syringe. In order to insure free movement of the syringe within the aperture 510, it is preferred to slightly oversize this aperture by an amount which may be determined by fitting the syringe barrel into the aperture in its position of use and then testing the degree of rotation of the barrel axis relative to the plane of the disc to see if a proper fit has been obtained. A degree of rotation between 5 and 25 degrees of the shield with respect to the axis of the barrel of the syringe is suitable, while permissible rotations in the order of 10 to b 15 degrees are preferred.

The outer periphery of the disc should be of a diameter sufficient to shield at least the user's fingers while disposed on either side of the syringe barrel, and while supporting the disc in a substantially horizontal position while grasping the syringe. Depending upon the size of the user's fingers and hand, a disc having a diameter of between 8 and 17 centimeters is acceptable, while preferred diameters range between 11 and 15 centimeters. Excellent results have been obtained using a disc having a 13 centimeter diameter. Since syringe barrel sizes vary substantially, in accordance with this embodiment of the present invention, a radio-pharmacist may equip his facility with a plurality of discs, each of which has apertures which are sized and, if preferred, coded for use with given syringe barrel sizes. In this manner, apertures need not be used which are oversized beyond the tolerances above described. Regardless of the thickness of the disc selected for use in accordance with the present invention, it is anticipated that in every instance the central aperture should be at least about 0.5 millimeters larger than the outer diameter of the syringe barrel. If desired, larger apertures may be provided to permit syringes to be accepted with their needle covers in place.

As used herein the terms "shielding material", "high density material", and "absorbent material" are intended to refer to materials having generally high atomic numbers (Z), such as lead, copper and tungsten, and more particularly to materials which have in their utilized thickness, half value layers of at least 3, and preferably 4-6. As used in the present application, the term "low density materials", is intended to refer to materials having low atomic numbers (Z), which are not particularly good absorbers of radiation, and, which, in their utilized thicknesses have half value layer values of less than one.

We claim:

1. A syringe shield for use with a syringe at least during the use of that syringe for drawing aliquots of radioactive materials from the mouth of a vial having a vial shield surrounding at least a portion of said mouth; comprising:
   a. a substantially tubular body means for receiving at least the barrel portion of said syringe; and
   b. radioactive material detection means disposed with said body means for detecting the radioactivity of the aliquot drawn into the barrel of said syringe.

2. The invention of claim 1 wherein said syringe shield further comprises dosage calibration means connected to said shield to calibrate the dosage of radioactive materials contained within said syringe.

3. The invention of claim 1 wherein said radioactive material detection means comprises a radio-florescent material disposed adjacent to said barrel.

4. The invention of claim 3 wherein said dosage calibration means comprises light transmission means for transmitting light generated by said radio-florescent material.

5. The invention of claim 4 wherein said dosage calibration means comprises light quantification means for determining and indicating the amount of radioactivity of said material within said barrel.

6. The invention of claim 1 wherein said radioactive material detection means comprises an ionization chamber radiation detector.

7. The invention of claim 1 wherein said radioactive material detection means comprises a solid state radiation detector.

8. A syringe shield for use with a syringe at least during the use of that syringe for drawing aliquots of radioactive materials from the mouth of a vial having a vial shield surrounding at least a portion of said mouth; comprising:
   a. a substantially tubular body means for receiving at least the barrel portion of said syringe, wherein said body means defines a viewing aperture, at least the interior surface of said body means disposed opposite from said aperture being a material which optically contrasts with the volumetric markings of said syringe; and
   b. a mouth shield means connected to a first end of said body means, extending transversely away from said body means for a preselected distance to substantially shield at least said mouth of said vial at least during said drawing of said aliquots.

9. A hand shield for use with a syringe at least during the use of that syringe for drawing aliquots of radioactive materials from a vial, comprising a shielding disc comprising a plurality of layers of material, at least one of which is a shielding material, said disc having an aperture centrally defined therein for receiving a syringe barrel therethrough.

10. The invention of claim 9 wherein the exterior surfaces of said disc are covered with a non-toxic material.

11. A radioactive dosage calibration apparatus, comprising:
   a. a syringe shield having a radiation detector means disposed therein for detecting radiation emitted from material contained within a syringe disposed therein; and
   b. a calibration means for calibrating and indicating the radioactivity of materials contained within said syringe in response to the radioactivity detected by said radiation detector means.

* * * * *

UNITED STATES PATENT AND TRADEMARK OFFICE
CERTIFICATE OF CORRECTION

PATENT NO. : 4,307,713
DATED : December 29, 1981
INVENTOR(S) : Galkin et al

It is certified that error appears in the above-identified patent and that said Letters Patent are hereby corrected as shown below:

Column 9, line 2, please delete "b".

Signed and Sealed this

Twenty-second Day of June 1982

[SEAL]

Attest:

Attesting Officer

GERALD J. MOSSINGHOFF
Commissioner of Patents and Trademarks